United States Patent [19]

Lewis

[11] 4,113,690

[45] Sep. 12, 1978

[54] SILICONE ELASTOMERS CONTAINING ALKOXYSILOXANOLS

[75] Inventor: Richard Newton Lewis, Tecumseh, Mich.

[73] Assignee: SWS Silicones Corporation, Adrian, Mich.

[21] Appl. No.: 769,062

[22] Filed: Feb. 16, 1977

Related U.S. Application Data

[60] Continuation-in-part of Ser. No. 645,734, Dec. 31, 1975, abandoned, Division of Ser. No. 435,151, Jan. 24, 1975, Pat. No. 3,979,546, which is a division of Ser. No. 214,406, Dec. 30, 1971, Pat. No. 3,799,962.

[51] Int. Cl.$^2$ .............................................. C08L 00/00
[52] U.S. Cl. .................... 260/37 SB; 260/448.8 R; 528/14

[58] Field of Search ...................... 260/46.5 R, 37 SB

[56] References Cited

U.S. PATENT DOCUMENTS 3,417,047  12/1968  Golitz et al. .................... 260/46.5 R Primary Examiner—Paul F. Shaver

[57] ABSTRACT

Alpha-alkoxy-omega-siloxanols, R'O(R$_2$SiO)$_x$H, are produced by contacting cyclic siloxanes with alcohols under mild conditions. For example, hexamethylcyclotrisiloxane heated at reflux in methanol for four hours gives 5-methyoxyhexamethyltrisiloxan-1-ol in high yield. The reaction proceeds more rapidly in the presence of weak acids or bases. The products are useful as coupling agents, as antistructure agents and filler-treating agents for silicone elastomers.

8 Claims, No Drawings

SILICONE ELASTOMERS CONTAINING ALKOXYSILOXANOLS

This is a continuation-in-part application of my copending application Ser. No. 645,734 filed on Dec. 31, 1975, now abandoned, which was a divisional application of application Ser. No. 435,151 filed on Jan. 24, 1975, now U.S. Pat. No. 3,979,546, which was a divisional application of application Ser. No. 214,406 filed Dec. 30, 1971, now U.S. Pat. No. 3,799,962.

The present invention relates to alkoxysiloxanols and more particularly to alpha-alkoxy-omega-siloxanols. Such materials contain one relatively more reactive group (OH) and one relatively less reactive group (alkoxy); for this reason they have long been sought as intermediates in the synthesis of siloxanes. They have not, however, been available by any process known heretofore.

Several processes that might have been expected to lead to alkoxysiloxanols have instead produced other products. For example, linear and cyclic methylpolysiloxanes heated with methanol in the presence of potassium hydroxide gave instead trimethylalkoxysilanes and dimethyldimethoxysilanes (U.S. Pat. Nos. 2,746,982 and 2,825,599). Cyclic trisiloxanes heated with n-octyl alcohol and toluenesulfonic acid in xylene gave dioctyloxytrisiloxanes and water as the principal products, even when the reaction was stopped at an early stage. [See Sprung and Guenther, J. Org. Chem. 26, 552 (1961)].

It is an object of this invention to provide alkoxysiloxanols. Another object of this invention is to provide alpha-alkoxy-omega-siloxanols. It is also an object of this invention to provide a method of producing alpha-alkoxy-omega-siloxanols in high yield and in a high state of purity. It is a further object of this invention to provide silicone elastomers containing novel antistructure agents.

These objects, and other which will become apparent from the following description, are achieved, generally speaking, by contacting a cyclic polysiloxane with an alcohol having up to 20 carbon atoms under relatively mild conditions to form alkoxysiloxanols of the general formula $R'O(R_2SiO)_xH$, wherein R and R' are organic radicals and x is an integer of at least 2 and preferably from 2 to 10. In some cases satisfactory results are obtained without a catalyst. In other cases it is advantageous to employ a weak base or a weak acid as a catalyst. These alkoxysiloxanols are incorporated in filled silicon elastomers to prevent structure buildup.

The cyclic polysiloxanes that may be used in the practice of this invention have the general formula $(R_2SiO)_y$. The radicals represented by R in this formula are hydrocarbon radicals, halogenated hydrocarbon radicals or cyanoalkyl radicals having from 1 to 8 carbon atoms. Suitable radicals include alkyl radicals such as methyl, ethyl, propyl, butyl or hexyl and fluorinated derivatives thereof; alkenyl radicals such as vinyl or allyl; and aryl radicals such as phenyl or tolyl and chlorinated derivatives thereof. It is preferred that at least half of the radicals be methyl radicals. Very good results are obtained if all of the radicals are methyl.

The number of units, y, in the cyclic polysiloxane is at least 3 and may be as high as 10. Generally the fastest an cleanest reaction occurs when y is 3. However, very good results are also obtained when y is 4 or 5 or even more. Suitable cyclic polysiloxanes thus include those of the general formula $[(CH_3)_2SiO]_y$, where y is a number from 3 to 10, particularly where y is 3, 4 or 5. Other cyclic polysiloxanes that may be used include those having groups other than methyl; for example, trimethyltrivinylcyclotrisiloxane, tetramethyltetravinylcyclotetrasiloxane, heptamethylvinylcyclotetrasiloxane, trimethyltriethylcyclotrisiloxane, trimethyltriphenylcyclotrisiloxane, hexaphenylcyclotrisiloxane, and the like.

Alcohols of almost every description may be used in the practice of this invention. Long-chain or short-chain alkyl, cycloalkyl, alkenyl and aralkyl alcohols and substituted derivatives thereof having up to 20 carbon atoms, including allyl alcohol and benzyl alcohol may be used. Substituted alcohols such as ethanolamine, 2-methoxyethanol, and 2-chloroethanol may also be used. Best results are usually obtained with the short-chain primary and secondary alcohols having up to 4 carbon atoms, e.g. methyl, ethyl, n-propyl, isopropyl, n-butyl, or isobutyl alcohol. The cleanest and fastest reactions, with fewest side reactions, occur with methyl alcohol.

The general reaction may be expressed by the equation $R'OH + (R_2SiO)_y \rightarrow R'O(R_2SiO)_xH$. In this equation R' represents the radical of an alcohol having up to 20 carbon atoms. Generally x is equal to y. Under certain conditions, x may have values greater than or less than y. It is preferred to work with a large excess of the alcohol, or the reaction may be very slow. Mole ratios of alcohol to cyclic polysiloxane should be between 2:1 and 50:1, preferably at least 5:1. Ratios higher than 50:1 may be employed, but offer no special advantage.

Reaction temperature is not critical. A reasonable rate of reaction can usually be achieved at room temperatures or below. Often it is preferred to operate at somewhat higher temperatures, but generally not much over 100° C. The reflux temperature of the alcohol is often a satisfactory operating temperature. If higher temperatures are desired, the reactions may be conducted under moderate pressure, but this is not usually necessary.

In some instances, as in the reaction of methanol with a cyclic trisiloxane, no catalyst is required, and the reaction proceeds at a satisfactory rate at the reflux temperature of the methanol.

When a catalyst is desired a weak acid or a weak base may be added, as indicated above. Strong acids such as toluenesulfonic acid and strong bases such as sodium methoxide are completely unsatisfactory as they cause unwanted cleavage and equilibration reactions. Even moderately strong acids such as oxalic acid ($pK_a$ 1.23) cause rapid decomposition of the alkoxysiloxanol that is produced and are of borderline utility. For optimum utility the catalyst should have a $pK_a$ or $pK_b$ above 1.5, corresponding to an acid or basic dissociation constant below 0.03. Maleic acid ($pK_a$ 1.83) and phosphoric acid ($pK_a$ 2.12) are about the strongest acids that can be used with safety. Even so they must be quickly neutralized when the desired reaction has been essentially completed. In general, any organic or inorganic acid or base may be used if its $pK_a$ or $pK_b$ lies between 1.5 and 10. Extremely weak acids or bases with pK values above 10 are relatively ineffective.

In order to eliminate the neutralization step, it is advantageous to use an acid or base that is volatile, so that it can be removed by distillation. A catalyst that decomposes into harmless by-products on heating is also desirable. Suitable acid catalysts include formic acid ($pK_a$ 3.75), acetic acid ($pK_a$ 4.75), propionic acid ($pK_a$ 4.87), malonic acid ($pK_a$ 2.83), succinic acid ($pK_a$ 4.16), and cyanoacetic acid ($pK_a$ 2.45).

Suitable bases include the primary, secondary, and tertiary aliphatic amines, which have $pK_b$ values in the range of about 1.95 (diisopropylamine) to 4.26 (trimethylamine); ammonia ($pK_b$ 4.75); ethanolamine and its alkyl derivatives; pyrrolidine, piperidine, and their homologs; morpholine ($pK_b$ 5.4), N-methylmorpholine ($pK_b$ 6.5), and N-ethylmorpholine ($pK_b$ 6.2); ethylenediamine ($pK_b$ 4.07) and its N-alkyl derivatives; piperazine ($pK_b$ 4.1) and dimethyl-piperazine ($pK_b$ 5.8); pyridine ($pK_b$ 8.77); and aromatic amines such as dimethylamine ($pK_b$ 8.94). Ammonia and the more volatile amines are particularly preferred because of their easy removal.

Salts of weak acids and bases may also be used, but they are less easily removed than the acids and bases listed above, and are therefore not usually preferred.

The catalysts listed above are effective at relatively low concentrations. Concentrations up to five percent may be used, but the preferred range is from 0.01 to 1.0, percent.

In order to purify the alkoxysiloxanols the excess of alcohol is removed by distillation at atmospheric or reduced pressure. Unreacted cyclic polysiloxane, if any, is best removed by vacuum distillation. The alkoxysiloxanol left in the distillation pot at this stage is often pure enough for most purposes. Further purification, if desired, may be achieved by distilling the alkoxysiloxanol at reduced pressure. Products of essentially 100 percent purity can thus be obtained.

The alkoxysiloxanols of this invention are useful as chemical intermediates, as antistructure agents in silica-filled silicone elastomers and as agents for reducing the surface reactivity of inorganic fillers, especially siliceous fillers. Suitable treated fillers may be obtained by heating untreated fillers with alkoxysiloxanols, preferably in the range of from 50° C to 200° C. The hydrophobic fillers thus obtained are very useful in the preparation of high-strength silicone elastomers.

The silicone elastomers of this invention are made by incorporating an alkoxysiloxanol as described above with a silicone gum and a reinforcing filler.

The silicone gum may be described as a polydiorganosiloxane having recurring structural unit of the formula

wherein the radicals represented by R", which may be the same or different, are monovalent hydrocarbon radicals or substituted hydrocarbon radicals of up to 8 carbon atoms. Suitable hydrocarbon radicals include alkyl radicals such as methyl, ethyl, butyl, and hexyl; alkenyl radicals such as vinyl; and aryl radicals such as phenyl and tolyl. Suitable substituted hydrocarbon radicals include halogenated radicals such as trifluoropropyl, chlorophenyl and dichlorophenyl, and cyanated radicals such as cyanoethyl, cyanopropyl and cyanophenyl. At least half of the radicals should be methyl; in many cases all of the radicals are methyl with the exception of a small proportion, not exceeding about 1 percent of vinyl radicals.

The silicone gum may be a homopolymer, such as poly(methyltrifluoropropylsiloxane) poly(methylcyanoethylsiloxane), or poly(methylphenylsiloxane), or a copolymer of dimethylsiloxane with a siloxane of the formula R"$_2$SiO in which one or both R" radicals are other than methyl.

End groups, not shown in the above formula are of secondary importance and their nature is not critical. Examples of suitable end groups include hydroxy; alkoxy, e.g. methoxy and ethoxy; and trisubstituted siloxy, e.g. trimethylsiloxy, dimethylvinylsiloxy, and methyldiphenylsiloxy.

The number of recurring units in the polydiorganosiloxane should be at least 2000. More specifically it should be sufficient to provide a plasticity as measured by the Williams Plastometer of from 45 to 240 and more preferably from 50 to 120.

The alkoxysiloxanols of this invention are employed in an amount of from 1 to about 30 percent and more preferably from 2 to 10 percent by weight based on the weight of the silicone gum.

Any of the conventional reinforcing fillers may be incorporated in the silicone elastomer. Among the fillers which may be employed are fumed and precipitated silicas, such as Cab-O-Sil, QUSO, Hi-Sil, Santocel, diatomaceous earths, clays, lithopone, ferric oxide, titanium dioxide, talc, zinc oxide, various forms of carbon, etc. The filler may be incorporated in amounts ranging from about 5 to 150 percent, preferably from about 10 to 100 percent by weight based on the weight of the silicone gum.

The silicone elastomer may be cured in the presence of peroxide vulcanizing agents. Examples of suitable vulcanizing agents are organic peroxides such as tertiary butyl perbenzoate, benzoyl peroxide, di-t-butyl peroxide, 2,4-dichlorobenzoyl peroxide, 2,5-bis(t-butylperoxy)-2,5-dimethylhexane and the like. Preferably the vulcanizing agent should be employed in an amount of from about 0.5 to 5 parts per 100 parts of the silicone gum.

When the alkoxysiloxanols are incorporated in the silicone elastomer, the composition remains millable indefinitely. The effect of the alkoxysiloxanols is independent of the order in which it is added to the composition. For example, the alkoxysiloxanol may be added to the filler and thereafter incorporated into the silicone gum. Alternatively, the alkoxysiloxanol may be combined with the silicone gum and the filler added thereafter. Also, the alkoxysiloxanol and filler may be added simultaneously to the polysiloxane. If desired, a solvent may be employed to aid in the dispersion of the alkoxysiloxanols, although there is no particular advantage in employing solvents. The vulcanizing agent can be added to the mixture at any time.

The above ingredients may be mixed in any desired fashion, although excellent results are obtained by milling.

The compounded materials are converted into cured silicone elastomers by heating at a temperature of at least 100° C i.e. at or above the decomposition temperature of the vulcanizing agent, until a nontacky coherent material is obtained. Generally, a heating time of from 3 to 30 minutes is sufficient. Thereafter, the vulcanized elastomer may be further cured by heating at temperatures up to 250° C.

Alkoxysiloxanols that contain vinyl groups, e.g. 5-methoxytrimethyltrivinyltrisiloxan-1-ol, are particularly useful as coupling agents between inorganic materials, such as fillers and fibrous reinforcing agents, e.g. glass fibers and organic polymers especially those that are cured by free-radical or vinyl-addition reactions.

Examples include silica-reinforced elastomers of various types and glass-reinforced polyesters.

The following examples are offered by way of illustration, but not by way of limitation. In these examples the dimethylsiloxane unit, $(CH_3)_2SiO$, is represented by the symbol D, and the methylvinylsiloxane unit, $CH_3C_2H_3SiO$, is represented by the symbol $D^v$. All parts are by weight unless otherwise specified.

EXAMPLE 1

Hexamethylcyclotrisiloxane ($D_3$) (22.2 parts) was dissolved in 120 parts of methanol and heated at refulx for 4 hours. Analysis by gas chromatography showed, in addition to methanol, 91.0 percent 5-methoxy-hexamethyltrisiloxan-1-ol ($CH_3OD_3H$), 7.5 percent unreacted $D_3$, and 1.5 percent 3-methoxy-tetramethyldisiloxan-1-ol ($CH_3OD_2H$), the latter indicating a slight amount of additional cleavage of the trisiloxanol. There was no evidence of symmetrical siloxanes such as a dimethoxytrisiloxane or a trisiloxanediol. On distillation at reduced pressure a nearly pure fraction of $CH_3OD_3H$ was obtained boiling at 86° C (15 mm). Absorption in the near infrared showed strong, sharp OH peaks at 2700 mm. and 2900 mm. Nuclear magnetic resonance showed the group ratios $CH_3(Si)$ 6.0, $CH_3O$ 1.1, OH 1.0; theoretical 6:1:1.

EXAMPLE 2

Ten parts of 1,3,5-trimethyl-1,3,5-trivinylcyclotrisiloxane ($D^v_3$) was mixed with 70 parts of methanol and 0.35 parts of formic acid and allowed to stand at room temperature for 4 days. The methanol was then removed under vacuum below room temperature, and the remainder was distilled at 1.6mm., giving 8.1 parts of a product boiling at 78°–89° C. Analysis by gas chromatography of the product showed 7.6 percent of 3-methoxy-1,3-dimethyl-1,3-divinyldisiloxan-1-ol ($CH_3OD^v_2H$), 21.5 percent of $D^v_3$, 68.9 percent of 5-methoxy-1,3,5-trimethyl-1,3,5-trivinylsiloxan-1-ol ($CH_3OD^v_3H$), and 2.0 percent of $CH_3OD^v_4H$.

EXAMPLE 3

Octamethylcyclotetrasiloxane ($D_4$) (11 parts) was heated to reflux with 60 parts of methanol and 0.4 parts of formic acid for 16 hours. Gas chromatographic analysis showed 29.7 percent of 7-methoxyoctamethyltetrasiloxan-1-ol ($CH_3OD_4H$), 1.0 percent of $CH_3OD_3H$, 0.1 percent of $CH_3OD_2H$, 68.7 percent of unreacted $D_4$, and 0.5 percent of a volatile compound, possibly $CH_3ODH$. The rate of formation of $CH_3OD_4H$ is thus about 2 percent per hour at 65° C, with very little by-product.

EXAMPLE 4

One part of decamethylcyclopentasiloxane ($D_5$) was mixed with 6 parts of methanol and 0.07 parts of cyanoacetic acid and kept at room temperature for 48 hours. At the end of this time 6.7 percent of the $D_5$ had been converted to 9-methoxydecamethylpentasiloxane-1-ol ($CH_3OD_5H$) with no by-products detectable at a level of 0.02 percent. This is a conversion of 3.4 percent per day.

A similar reaction was carried out with 0.15 parts of di-n-butylamine. A smaller amount of $CH_3OD_5H$ was produced, along with significant amounts of $CH_3OD_4H$, $CH_3OD_3H$, and $CH_3OD_2H$. In this example the acid catalyst appears to give fewer by-products.

EXAMPLE 5

One part of $D_3$ was mixed with 7 parts of ethyl alcohol and 0.05 arts of formic acid at room temperature. In 6 hours gas chromatography showed the following (in addition to ethyl alcohol): unreacted $D_3$ 71.0 percent, $C_2H_5OD_3H$ 18.3 percent, a more volatile by-product 3.8 percent, and a less volatile by-product 6.9 percent.

EXAMPLE 6

Eleven parts of $D_3$, 60 parts of n-propyl alcohol and 0.4 parts of formic acid were heated at reflux (95° C) for 1 hour, producing a major amount of $C_3H_7OD_3H$ and minor amount of two less volatile materials.

EXAMPLE 7

Eleven parts of $D_3$, 60 parts of methanol, and 0.6 parts of acetic acid were heated at reflux (65° C) for 2 hours. At this time 98 percent of the $D_3$ had been converted to $CH_3OD_3H$, with only traces of by-products ($CH_3OD_2H$ and $CH_3OD_4H$). In comparison with a similar reaction without a catalyst (Example 1) it is clear that the reaction in the presence of acetic acid is not only faster but produces fewer by-products.

EXAMPLE 8

Example 7 was repeated with 0.4 parts of formic acid in place of acetic acid, and the reaction was about 96 percent complete in 12 minutes, again with practically no by-products. When reflux was continued for 90 minutes, small amounts of $CH_3OD_2H$, $CH_3OD_4H$ and $CH_3OD_6H$ were formed.

EXAMPLE 9

Example 7 was repeated with 0.5 parts of N,N'-dimethylpiperazine as a catalyst. The reaction was 80 percent complete in 10 minutes with only traces of by-products. After 2.5 hours of reflux significant amount of $CH_3OD_2H$, $CH_3OD_4H$, $CH_3OD_5H$, and $CH_3OD_6H$ were formed, $CH_3OD_3H$ still being the major product.

EXAMPLES 10 –12

Solutions of 9 parts of $D_3$ in 60 parts of methanol were prepared at room temperature. To these were added 0.5 parts of cyanoacetic acid, 0.15 parts of ammonia, and 0.3 parts of di-n-butylmine. All were effective catalysts and produced 90 percent yields of $CH_3OD_3H$ in less than 30 minutes. In each case significant by-products appeared only after several hours.

Identification of the minor ingredients in the above examples (1 –12) was made on the basis of gas chromatography. A Varian Aerograph Model 700 Gas Chromatograph was used. The column used has the following description:

| | |
|---|---|
| Material: | Stainless Steel |
| Dimensions: | 5 feet × ¼ inch O.D. |
| Liquid phase: | Dimethyl silicone gum (SE-30), 30 percent |
| Solid support: | 70 – 80 mesh acid-washed dimethyldichlorosilane-treated firebrick (Gas-chrom) (RZ), 70 percent. |
| Helium flow: | 60 ml/min. |

The retention times given below are those actually measured. They were reproducible within 1 percent using the above column, although another column might have given somewhat different values. However, the important consideration is relative, rather than absolute retention times. Thus it is known that in a homologous series the ratio of retention times is constant from one member to the next.

| Retention Times at 170° C.[a] | | |
|---|---|---|
| Compound | Retention Time, Minutes | Ratio[b] |
| $D_3$ | 1.35 | — |
| $D_4$ | 2.80 | 2.07 |
| $D_5$ | 5.83 | 2.08 |
| $D_6$ | 12.70 | 2.18 |
| Average ratio for D Cyclics | | 2.11 |
| $CH_3OD_2H$ | 1.46 | — |
| $CH_3OD_3H$ | 3.24 | 2.24 |
| $CH_3OD_4H$ | 6.09 | 2.13 |
| $CH_3OD_5H$ | 14.08 | 2.15 |
| $CH_3OD_6H$ | 31.02 | 2.11 |
| $CH_3OD_7H$ | 64.00 | 2.05 |
| Average ratio for $CH_3OD_xH$ | | 2.14 |
| $HOD_3H$ | 3.43 | — |
| $CH_3OD_3H$ | 3.24 | 0.94 |
| $C_2H_5OD_3H$ | 4.08 | 1.26 |
| $C_3H_7OD_3H$ | 5.05 | 1.35 |

[a]Retention times relative to air.
[b]Retention time divided by that of next lower homolog.

It is evident from the data above that the effect of an added D unit in a methoxysiloxanol is almost identical to its effect in the know series of cyclic siloxanes. This regularity provides an invaluable aid of identification. The same is not true in the series $HOD_3H$, $CH_3OD_3H$, $C_2H_5OD_3H$, $C_3H_7OD_3H$, in which the homologous change involves a relatively small part of the molecule.

| Retention Times at 190° C | | |
|---|---|---|
| Compound | Retention Time, Minutes | Ratio |
| $D'_3$ | 2.52 | — |
| $D'_4$ | 6.08 | 2.42 |
| $D'_5$ | 14.77 | 2.43 |
| $CH_3OD'_2H$ | 2.0 | — |
| $CH_3OD'_3H$ | 5.38 | 2.69 |
| $CH_3OD'_4H$ | 13.04 | 2.45 |

EXAMPLE 13

A. One hundred parts of a silicone gum (containing 0.1 percent of methylvinylsiloxane) was mixed with 10 parts of $CH_3OD_3H$ and 36 parts of fumed silica (Cab-O-Sil HD-5) in a Sigma mixer at 250° C. No difficulty was encountered and a smooth compound was obtained.

B. A similar compound was prepared with only 6 parts of $CH_3OD_3H$. Some mixing difficulty was encountered, but a smooth compound was eventually obtained.

C. A reference compound was prepared from 100 parts of the same gum, 16 parts of a standard "softner" (antistructure agent) composed of a linear polydimethylsiloxane containing 2.5 percent of OH groups, and 36 pars of Cab-O-Sil HS-5. Attempts to prepare similar compounds with less than 16 parts of the standard softener were unsuccessful because of structure build-up. Thus it is apparent that $CH_3OD_3H$ is approximately twice as effective, on a weight basis, as the standard softener.

Samples of each of the above were successfully cured by heating with dichlorobenzoyl peroxide (1.1 percent of a 50-percent paste, 5 minutes at 240° F). The following physical test data were obtained after a 16-hour postcure at 450° F.

| | A | B | C |
|---|---|---|---|
| Hardness, Shore A | 43 | 52 | 50 |
| Tensile strength, psi | 1200 | 1000 | 1100 |
| Elongation, percent | 475 | 400 | 500 |
| Compression set (ASTM D395 Method B) | 23 | 18 | 30 |

It can be seen from these data that the physical properties are approximately equivalent, in general. However, the better (lower) compression set values of the elastomers containing the methoxysiloxanol are clearly evident.

EXAMPLE 14

Six drops of $CH_3OD_3H$ were applied to the surface of a clean glass plate. After 10 minutes at room temperature the surface was washed off with acetone and found not to be water repellent. A second glass plate was treated with six drops of $CH_3OD_3H$ and heated 15 minutes at 105° C. The liquid had evaporated and the surface was found to be somewhat water repellent; water drops on the surface formed a contact angle of about 60°. A third glass plate was treated with 6 drops of $CH_3OD_3H$ and heated for 30 minutes at 150° C, whereby it became water repellent; water drops formed contact angles of about 70° on the surface.

EXAMPLE 15

A fumed silica (Cab-O-Sil MS-7) was mixed with one tenth its weight of $CH_3OD_3H$ and allowed to stand for 16 hours at room temperature. It was not visibly altered and was easily dispersed in water. A similarly treated silica heated for one hour at 100° C in a closed container became highly hydrophobic and could not be dispersed in water.

EXAMPLE 16

A precipitated calcium polysilicate (Hi-Sil 404) (1.0 part) was heated with 0.15 part of $CH_3OD_3H$ in a closed bottle at 95° C for two hours, at the end of which it was completely hydrophobic.

Although specific examples are mentioned and have been herein described, it is not intended to limit the invention solely thereto but to include all the variations and modifications falling within the spirit and scope of the appended claims.

What is claimed is:

1. An improved composition containing a silicone gum and a reinforcing filler, the improvement which comprises incorporating in said composition from 1 to 30 percent by weight based on the weight of the silicone gum of an alpha-alkoxy-omega-siloxanol of the formula $R'O(R_2SiO)_xH$, in which R is selected from the class consisting of monovalent hydrocarbon radicals, halogenated monovalent hydrocarbon radicals and cyanoalkyl radicals having from 1 to 8 carbon atoms, R' is an alkyl radical having up to 4 carbon atoms, and x is an integer of from 2 to 10.

2. The improved composition of claim 1, wherein the alpha-alkoxy-omega-siloxanol is 5-methoxyhexamethyltrisiloxan-1-ol.

3. The improved composition of claim 1, wherein the alpha-alkoxy-omega-siloxanol is 7-methoxyoctamethyltetrasiloxan-1-ol.

4. The improved composition of claim 1, wherein the alpha-alkoxy-omega-siloxanol is 9-methoxydecamethylpentasiloxan-1ol.

5. The improved composition of claim 1, which contains a peroxide vulcanizing agent.

6. The improved composition of claim 5, wherein the vulcanizing agent is dichlorobenzoyl peroxide.

7. The improved composition of claim 5, wherein the peroxide vulcanizing agent is 2,5-bis-(t-butylperoxy)-2,5-dimethylhexane.

8. A silicone elastomer which is obtained by heating the composition of claim 5 at the decomposition temperature of the vulcanizing agent.

* * * * *